United States Patent [19]

Gries et al.

[11] Patent Number: 4,925,652

[45] Date of Patent: *May 15, 1990

[54] NITROXYL COMPOUNDS, AND DIAGNOSTIC MEDIA BASED THEREON USEFUL FOR ENHANCING NMR IMAGING

[75] Inventors: Heinz Gries; Ulrich Niedballa; Hanns-Joachim Weinmann, all of Berlin, Fed. Rep. of Germany

[73] Assignee: Schering Aktiengesellschaft, Berlin and Bergkamen, Fed. Rep. of Germany

[ * ] Notice: The portion of the term of this patent subsequent to Jul. 4, 2006 has been disclaimed.

[21] Appl. No.: 637,085

[22] Filed: Aug. 3, 1984

[30] Foreign Application Priority Data

Aug. 3, 1983 [DE] Fed. Rep. of Germany ....... 3328365

[51] Int. Cl.$^5$ .................. A61K 49/00; G01N 31/00
[52] U.S. Cl. .................. 424/9; 514/212; 514/277; 514/315; 514/408; 514/426; 530/350
[58] Field of Search .............. 260/239 BE, 239 BF, 260/239 B; 546/244, 247, 309, 306; 548/557, 565, 568; 514/183, 212, 277, 315, 408, 426; 424/9; 530/350

[56] References Cited

U.S. PATENT DOCUMENTS

| | | | |
|---|---|---|---|
| 3,959,287 | 5/1976 | Goldstein et al. | 436/803 |
| 4,656,026 | 4/1987 | Coffman et al. | 424/9 |
| 4,834,964 | 5/1989 | Rosen | 424/4 X |
| 4,845,090 | 7/1989 | Gries et al. | 514/277 X |

FOREIGN PATENT DOCUMENTS

| | | |
|---|---|---|
| 8633082 | 1/1983 | Australia . |
| 1501115 | 10/1967 | France . |
| 1570560 | 3/1968 | France . |
| 2235103 | 6/1973 | France . |

OTHER PUBLICATIONS

Rosen: Official Gazette (USPTO), 5/30/89, Pat. #4834964.
Rosen: Chemical Abstracts, 109: 34592d (1988).
Brasch-II Radiology 147, 781-788, (1983).
"Brasch, An Overview of Contrast Agents for Magnetic Resonance Imaging", *Overview of Contrast Agents for MRI*, pp. 11-13.
J. Comput. Assist. Tomogr., vol. 7, No. 1, 1983, p. 184.
Chem. Abstracts, 88, 134654s, 1978, p. 371.
Chem. Abstracts, 90, 137610b, 1979, p. 494.

Die Pharmazie, 35:1, Jan. 1980, pp. 10-14, Kertscher et al.
Synthesis, No. 7, Jul. 1975, pp. 462-463, Golding et al.
Biochemistry, 14, No. 12, 175, pp. 2754-2760, Johnston et al.
Griffeth, et al., Invest. Radiology, vol. 19, (1984), pp. 553-562.
Rosen et al., Biochem. Pharm., vol. 26, (1977), pp. 675-678.
Biological Magnetic Resonance, Berliner, et al. (eds.), vol. 4, Plenum Press, New York, (1982), pp. 1-11.
Bulletin of the Academy of Sciences of the USSR, Russian Original, vol. 24, No. 4, (Apr. 1975), pp. 859-862, Translated from Russian.
Kressel, H. Y., Magnetic Resonance Annual, (1985), Raven Press, pp. 231-266.
Brasch, et al., Radiology, vol. 147, (1983), pp. 773-779.
Keana, J. F., Chemical Reviews, vol. 78, (1978), pp. 37-64.

*Primary Examiner*—Robert J. Warden
*Assistant Examiner*—Richard Wagner
*Attorney, Agent, or Firm*—Millen, White & Zelano

[57] ABSTRACT

Diagnostic media suitable for NMR diagnoses contain compounds of Formula I

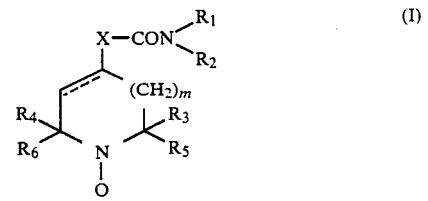

wherein
$=\!=\!=\!=\!=$ is a single bond or a double bond,
X is the grouping —$(CH_2)_n$— or, if $=\!=\!=\!=\!=$ is a single bond, also the grouping —$NHCO(CH_2)_n$— wherein n means 0 to 4,
m means the numbers 0, 1, or 2,
$R_1$ is an alkyl residue substituted by hydroxy groups, acyloxy groups and/or alkylidenedioxy groups,
$R_2$ has the same meanings as $R_1$ or is a hydrogen atom or an alkyl residue,
$R_3$ and $R_4$ are alkyl residues, and
$R_5$ and $R_6$ are alkyl residues optionally substituted by hydroxy groups.

30 Claims, No Drawings

NITROXYL COMPOUNDS, AND DIAGNOSTIC MEDIA BASED THEREON USEFUL FOR ENHANCING NMR IMAGING

The present invention relates to new compounds and new diagnostic media based thereon.

SUMMARY OF THE INVENTION

It is an object of this invention to provide new compounds having valuable pharmacological properties, e.g., for use in medical diagnoses.

Upon further study of the specification and appended claims, further objects and advantages of this invention will become apparent to those skilled in the art.

These objects have been attained by providing new diagnostic media comprising a compound of Formula I

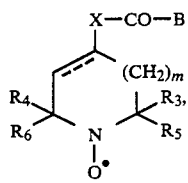 (I)

wherein

B is a protein, sugar, or lipid residue, or a group of the formula,

$===$ is a single bond or a double bond,

X is the grouping $-(CH_2)_n-$ or, if $===$ is a single bond, also the grouping $-NHCO(CH_2)_n-$ wherein n is 0 to 4, m is a number 0, 1, or 2, $R_1$ is an alkyl residue substituted by hydroxy groups, acyloxy groups and/or alkylidenedioxy groups, $R_2$ has one of the meanings for $R_1$ or is a hydrogen atom or an alkyl residue, $R_3$ and $R_4$ are alkyl residues, and $R_5$ and $R_6$ are alkyl residues optionally substituted by hydroxy groups.

They have also been attained by providing the corresponding compounds themselves except for 2,2,5,5-tetramethyl-3-pyrroline-1-oxyl-3-carboxylic acid (2-hydroxyethyl)amide and 2,2,5,5-tetra-methyl-3-pyrroline-1-oxyl-3-carboxylic acid (2,3-dihydroxypropyl)amide, which are known. See, e.g., Tetrahedron 33:2969 et seq., 1977.

DETAILED DISCUSSION

The compounds of Formula I carry as substituent B the residue of a protein, for example, an albumin, immunoglobulin, or monoclonal antibodies, that of a sugar, for example, glucose or a glucose derivative, that of a lipid, for example dipalmitoylphosphatidylethanolamine or the group $-NR_1R_2$.

The types of pharmacologically compatible protein, sugar and lipid biomolecules which can be used as B and the methods of bonding these biomolecules to the nucleus of the compounds of this invention are known and are exemplified herein.

The employed biomolecules are organspecific and are used as carriers for the paramagnetic nitroxyl moieties which are firmly bound to them by amide or ester linkages for instance. For example the following biomolecules are useful for in vivo diagnosis: glucose and deoxy-glucose for testing the cerebral regions (J. Nucl. Med. 1983, 24, 366), fluorodeoxy-glucose for testing ischemic conditions in the heart (ibid., 1060), amino acids for diagnosis of pancreatic disease (ibid., 121), fatty acids for testing myocardinal regions (ibid., 285) and cholesterol derivatives for testing of adrenal disorders (J. Med. Chem. 1982, 25, 618), which disclosure is incorporated by reference herein. Which biomolecule is used for a given purpose is readily determined conventionally and conventionally depends on the site of diagnosis desired, inter alia.

$R_1$ is an alkyl residue preferably of 2–8 carbon atoms and especially 2–6 carbon atoms, substituted by 1–5 hydroxy groups, 1–5 acyloxy groups, or 1–3 alkylidenedioxy groups. All of the carbon atoms of these alkyl residues can carry hydroxy groups, except for the carbon atom linked to the amide nitrogen. Suitable substituents $R_1$ include, for example: 2-hydroxyethyl, 2-hydroxypropyl, 2-hydroxy-1-methylethyl, 3-hydroxypropyl, 2,3-dihydroxypropyl, 2-hydroxy-1-(hydroxymethyl)-ethyl, 2-hydroxybutyl, 2,3-dihydroxybutyl, 2,3,4-trihydroxybutyl, 2,3-dihydroxy-1-hydroxymethylpropyl, 2,3,4,5-tetrahydroxypentyl, or 2,3,4,5,6-pentahydroxyhexyl. The hydroxy groups can be present in the free, esterified (acyloxy), or ketalized (alkylidenedioxy) form. Suitable esters are preferably those derived from an alkanecarboxylic acid of 2–6 carbon atoms, e.g., acetic acid, propionic acid, butyric acid, isobutyric acid, trimethylacetic acid, valeric acid, or caproic acide. Ketalized hydroxy groups include the acetonides, in particular. In general, ketal structures of the formula

wherein R is $C_{1-6}$-alkylene, optionally substituted by alkyl groups of 1–4 carbon atoms in total, are suitable.

The substituent $R_2$ can independently have one of the meanings given for the substituent $R_1$. However, preferably, $R_2$ is a hydrogen atom or an alkyl group of up to 4 carbon atoms, e.g., ethyl, propyl, isopropyl, or especially methyl.

The substituents $R_3$ and $R_4$ independently represent lower alkyl groups of 1–4 carbon atoms, e.g., ethyl, propyl, isopropyl, or especially methyl.

The substituents $R_5$ and $R_6$ independently preferably are alkyl as described for $R_3$ and $R_4$. However, they can also be alkyl groups of up to 4 carbon atoms substituted by 1–3 hydroxy groups, for example, hydroxymethyl, 1-hydroxyethyl, 2-hydroxyethyl, 1,2-dihydroxyethyl, 1-hydroxypropyl, 1,2-dihydroxypropyl, or 1,2,3-trihydroxypropyl.

The symbol m is preferably 0 or 1.

In the grouping $-(CH_2)_n-$, n preferably is 0 or 1; in the grouping $-NHCO(CH_2)_n-$, n preferably is 3 or 4 and, in particular, is 2.

It has now been found that the compounds used in the diagnostic media of this invention are surprisingly excellently suited for the production of diagnostic media useful in NMR diagnostics. For a great variety of purposes, there is a need, above all, for highly compatible and also stable, readily soluble and adequately selective NMR diagnostic agents. The novel compounds of Formula I described herein, especially those wherein the hydroxy groups are not present in esterified or ketalized form satisfy these requirements.

For example, the compounds of Formula I linked to proteins are suited particularly for tumor and infarction diagnostics. Especially suitable for liver and spleen analyses are, for example, lipid conjugates or clathrates with liposomes present, for example, as uni- or multilamellar phosphatidylcholine-cholesterol vesicles.

Suitable for analyses of cerebral regions are sugar-conjugates and for analyses of myocardial regions conjugates with fatty acids. Compounds wherein B is $NR_1R_2$ can be used for the assessment of kidney tumors. Compounds wherein B is an antibody are valuable for the diagnosis of tumors of the breast and of the colon, for instance.

The diagnostic media of this invention can be administered enterally or partenterally, especially intravenously, intraarterially, or intralumbarly.

They can be prepared conventionally, e.g., for compounds of Formula I wherein B is —NRhd $1R_2$—, by (a) oxidizing a compound of Formula II

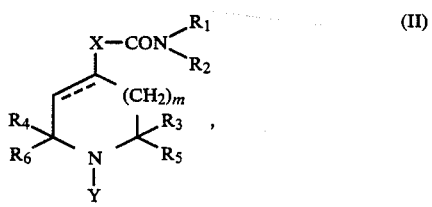

wherein

-----, m, X, $R_1$, $R_2$, $R_3$, $R_4$, $R_5$, and $R_6$ are as defined above, and Y is hydrogen or hydroxy, or (b) condensing a carboxylic acid of Formula III

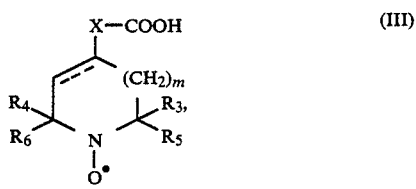

wherein -----, m, X, $R_3$, $R_4$, $R_5$ and $R_6$ are as defined above, or a conventional reactive derivative of this carboxylic acid, with an amine of Formula IV

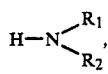

wherein $R_1$ and $R_2$ are as defined above, or (c) condensing a carboxylic acid of Formula V

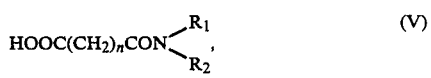

wherein n, $R_1$ and $R_2$ are as defined above, or a reactive derivative of this carboxylic acid, with an amine of Formula VI

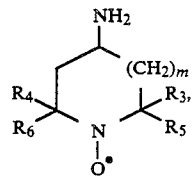

wherein m, $R_3$, $R_4$, $R_5$ and $R_6$ are as defined above, and optionally conventionally cleaving by hydrolysis any present ketal or acyl groups; and e.g., for the compounds of Formula I wherein B is a protein, sugar, or lipid residue, by conventionally reacting a carboxylic acid of Formula III wherein -----, m, X, $R_3$, $R_4$, $R_5$ and $R_6$ are as defined above, or a reactive derivative of this carboxylic acid, with a nucleophilic group of the protein, sugar, or lipid.

The nitroxyl compounds of Formula I wherein B is an —$NR_1R_2$— group can be prepared from the compounds of Formula II under conditions well known to those skilled in the art. Thus, the compounds of Formula II can be oxidized, for example, with hydrogen peroxide in the presence of tungstate catalysts, e.g., sodium tungstate. The oxidation is especially successful with organic peracids, such as perbenzoic acid, 3-chloroperbenzoic acid, and peracetic acid.

The formation of the amides from the corresponding carboxylic acids and amines likewise can be effected in a conventional procedure (Houben-Weyl), "Methoden der Organischen Chemie" Vol. 15/2, 1974, pp. 1 et seq). Thus, e.g., the carboxylic acids can be converted into the corresponding acid chloride or mixed anhydride (for example with trifluoroacetic acid anhydride or the methyl ester of chloroformic acid), and then this compound is reacted with the amine. It is furthermore also possible to condense both components in the presence of a dehydrating agent (such as N,N'-carbonyl diimidazole or dicyclohexyl carbodiimide).

The optionally following splitting off of the blocking groups likewise takes place in the conventional way. One good method is ketal splitting with acids and ester cleavage by means of alcoholic acids or bases.

The new hydroxyalkylamides are especially valuable in respect to their high in vivo stability concerning the nitroxyl function.

The formation of the conjugates with biomolecules is also conducted by following conventional methods, for example by reaction of the nucleophilic group of a biomolecule, such as the amino, phenol, sulfhydryl, or imidazole group, with an activated derivative of Formula III. Examples of activated derivative of Formula III. Examples of activated derivatives include acid chlorides, mixed anhydrides (see, for example, G. E. Krejcarek and K. L. Tucker, Biochem. Biophys. Res. Commun. 1977, 581), activated esters, nitrenes, or isothiocyanates.

A survey of those reactive groups suited for the attachment is given on page 11 of the DOS DE 3239410. (US 315286)

The starting compounds for the process of this invention all are known or can be prepared conventionally from known starting materials (see for example G. Sosnovsky, M. Konieczny, Z. Naturforsch. 32b, 328 [1977]).

It has been found that synthesis of the known compounds can frequently be done by a substantially simpler method than described in the literature, as can be seen from the preparations described below.

2,2,5,5-Tetramethylpyrroline-3-carboxylic Acid Methyl Ester

Under agitation and cooling at 10°–15° C., in portions, 118.19 g (300 millimoles) of 3,5-dibromo-2,2,6,6-tetramethylpiperidin-4-one hydrobromide is added to 1,200 ml of sodium methylate solution containing 20.69 g (900 millimoles) of sodium. After 30 minutes of agitation, the mixture is concentrated under vacuum, the residue is taken up in dry diethyl ether, filtered off from the solid matter, the solution is again concentrated under vacuum, and the residue is distilled with the aid of a water-jet aspirator.

The methyl ester of 2,2,5,5-tetramethyl-3-pyrroline-3-carboxylic acid passes over at 88–98/15 mm as a colorless fluid; yield: 54.2 g (91% of theory).

The compound is of 92.3% strength according to gas chromatogram, and of sufficient purity for further processing.

2,2,5,5-Tetramethyl-3-pyrroline-1-oxyl-3-carboxylic Acid Methyl Ester

A solution is prepared from 70 ml of dichloromethane and 13.38 g (73 mmol) of 2,2,5,5-tetramethyl-3-pyrroline-3-carboxylic acid methyl ester, combined with 0.1 g (1.2 mmol) of sodium acetate, cooled to $-10°$ C., and combined in incremental portions under agitation with a cooled solution of 30 g (146 mmol) of 37% strength peracetic acid containing another 0.8 g (9.6 mmol) of sodium acetate. After this adding step, the mixture is stirred for another 4 hours, then diluted with dichloromethane, and stirred into sodium bicarbonate solution to neutralize the acetic acid. The organic phase is separated, dried over sodium sulfate, and concentrated to dryness under vacuum. The methyl ester of 2,2,5,5-tetramethyl-3-pyrroline-1-oxyl-3-carboxylic acid is crystallized from diethyl ester in needles, mp 87°–89° C.

The yield is 12.63 g (87.3% of theory).

2,2,5,5-Tetramethyl-3-pyrroline-1-oxyl-3-carboxylic Acid

A solution of 15.10 g (76.17 mmol) of 2,2,5,5-tetramethyl-3-pyrroline-1-oxyl-3-carboxylic acid methyl ester in 40 ml of distilled water and 10 ml of ethanol was combined with 4.57 g (114.26 mmol) of sodium hydroxide in 40 ml of distilled water. The mixture is heated under agitation to 60° C. for 1.5 hours, diluted with 200 ml of water, acidified with 4N sulfuric acid to pH 3, and the acid is extracted with methylene chloride. The organic phase is dried over sodium sulfate and evaporated to dryness under vacuum. The 2,2,5,5-tetramethyl-3-pyrroline-1-oxyl-3-carboxylic acid is crystallized from ethanol/diethyl ether (mp 221°–223° C.). The yield is 13.82 g (98.5% of theory).

2,2,5,5-Tetramethylpyrrolidine-3-carboxylic Acid Methyl Ester 87.80 g (479 mmol) of 2,2,5,5-tetramethyl-3-pyrroline-3-carboxylic acid methyl ester is dissolved in 1,000 ml of methanol and hydrogenated in the presence of 11 g of Raney nickel at room temperature under an initial pressure of 180 bar. The mixture is removed from the catalyst by suctioning, the solution is treated with activated carbon, concentrated under vacuum, and the residue is distilled with the aid of a water-jet aspirator. The methyl ester of 2,2,5,5-tetramethylpyrrolidine-3-carboxylic acid passes over at 86°–87°/14 mm. Yield: 77.1 g (88% of theory). As per analysis by gas chromatography, the compound has a purity of 98.7%.

| $C_{10}H_{19}NO_2$ (185.27) | | | |
|---|---|---|---|
| Calculated: | 64.83 C | 10.34 H | 7.56 N |
| Found: | 64.71 C | 10.44 H | 7.44 N |

2,2,5,5-Tetramethylpyrrolidine-1-oxyl-3-carboxylic Acid Methyl Ester

A solution of 20.30 g (108.15 mmol) of 2,2,5,5-tetramethylpyrrolidine-3-carboxylic acid methyl ester (98.7% strength) in 200 ml of dichloromethane is combined with 0.14 g (1.6 mmol) of sodium acetate, and the solution is cooled to $-10°$ C. To the stirred solution are added dropwise 45.2 g (220 mmol) of peracetic acid (37% strength, 1% sulfuric acid), likewise cooled, as well as 1.22 g (14.7 mmol) of sodium acetate, suspended in the peracetic acid. The mixture is stirred overnight, the acetic acid is neutralized with sodium bicarbonate, the organic phase is separated, dried over sodium sulfate, and concentrated under vacuum. The residue is distilled by means of an oil pump. At 76°/0.01 torr, 20.23 g (93.4% of theory) of an orange-colored oil passes over.

| $C_{10}H_{18}NO_3$ (200.26) | | | |
|---|---|---|---|
| Calculated: | 59.98 C | 9.06 H | 6.99 N |
| Found: | 59.89 C | 9.17 H | 6.93 N |

2,2,5,5-Tetramethylpyrrolidine-1-oxyl-3-carboxylic Acid 8.75 g (218.87 mmol) of sodium hydroxide is dissolved in 120 ml of distilled water and combined with a solution of 29.22 g (145.91 mmol) of 2,2,5,5-tetramethylpyrrolidine-1-oxyl-3-carboxylic acid methyl ester in 20 ml of ethanol. The mixture is heated under agitation to 60° C. for 90 minutes, diluted with 200 ml of water, and acidified to pH 3 with 4N sulfuric acid. The acid is taken up in dichloromethane, the organic solution is dried over sodium sulfate and concentrated to dryness under vacuum. The residue is crystallized from dichloromethane/diethyl ether, thus obtaining 26.12 g (96.1% of theory) of 2,2,5,5-tetramethylpyrrolidine-1-oxyl-3-carboxylic acid, mp 197°–199° C.

| $C_9H_{16}NO_3$ (186.23) | . | | |
|---|---|---|---|
| Calculated: | 58.05 C | 8.66 H | 7.52 N |
| Found: | 58.11 C | 8.72 H | 7.35 N |

Succinic Acid (2,2,6,6-Tetramethyl-1-oxyl-4-piperidyl) Monoamide 55 g (=321 mmol) of 4-amino-2,2,6,6-tetramethyl-piperidin-1-oxyl is dissolved in 55 ml of pyridine. Under agitation, a solution of 40.7 g (407 mmol) of succinic anhydride in 500 ml of tetrahydrofuran is added dropwise thereto. The mixture is further stirred for 12 hours at room temperature and concentrated to dryness under vacuum. The residue is combined with 1,000 ml of water, and the aqueous solution is extracted with ether to remove the pyridine. The mixture is then concentrated to about 200 ml under vacuum and the thus-formed precipitate is suctioned off after several hours of stirring in an ice bath. After washing with a small amount of ice-cold water and drying at 40° C. under vacuum, 81.3 g (=93% of theory) of product is obtained as orange-colored crystals, mp 108°–110° C.

| $C_{13}H_{23}N_2O_4$ (271.34) | | | |
|---|---|---|---|
| Calculated: | 57.54 C | 8.54 H | 10.33 N |
| Found: | 57.48 C | 8.60 H | 10.41 N |

The compounds of this invention of Formula I provide valuable diagnostic agents. For practical application, they are conventionally dissolved or suspended in water or physiological salt solution and optionally converted into a form suitable for intravasal or oral administration, together with the additives customary in galenic pharmacy, so that their concentrations are in a range from 1 μmol/liter to 1 mol/liter. Precise concentrations and individual dosages are determined routinely using fully conventional considerations.

The compatibility of the novel diagnostic media is clearly superior to that of the known, comparable compounds. Toxic effects of the ions heretofore required for salt formation, such as sodium, potassium, meglumine, etc. are entirely or for the largest part eliminated. The osmotic pressure of the concentrated solutions of these diagnostic media is drastically reduced. Also, thereby the compatibility is substantially improved upon oral and parenteral administration since strongly hypertonic solutions damage blood vessels and tissue, affect the heart and the circulation, and evoke undesirable diuretic effects.

The compounds of this invention favorably affect the relaxation periods of the protons in the body from which NMR signals are derived. As compared with the known nitroxyl radicals, they exhibit a greater bioavailability and are substantially less toxic. This has been demonstrated by the following experiments.

Mice weighing 18–22 g were given varying quantities of the compound as a 0.5-millimolar aqueous solution per kg, adjusted to pH 7–7.5 by intravenous injection into the tail vein. After 7 days, the survival rate of the mice was determined and, from this value, the $LD_{50}$ in mmol/kg of animal was calculated in the usual way.

The table set forth below shows the thus-obtained results as compared with the previously known compounds 1 and 2. (J. Comput. Assist. Tomogr. 7, 1983, 184.)

| No. | Compound | $LD_{50}$ in mmol/kg Mouse |
|---|---|---|
| 1 | Succinic Acid (2,2,6,6-tetramethyl-1-oxylpiperidin-4-yl)-amide | 10 |
| 2 | 2,2,5,5-Tetramethylpyrrolidine-1-oxyl-3-carboxylic Acid | 10 |
| 3 | 2,2,5,5-Tetramethyl-3-pyrroline-1-oxyl-3-carboxylic Acid (1,3,4-Trihydroxybut-2-yl)amide | 20 |
| 4 | 2,2,5,5-Tetramethyl-3-pyrroline-1-oxyl-3-carboxylic Acid (2,3-Dihydroxypropyl)amide | 15 |
| 5 | 2,2,5,5-Tetramethylpyrrolidine-1-oxyl-3-carboxylic Acid (1,3,4-Trihydroxybut-2-yl)amide | 25 |

By this invention, novel diagnostic media have been successfully made available, opening up new possibilities in diagnostic medicine. This development is extremely desirable and necessary, above all, with respect to the development of novel imaging methods in medical diagnostics.

Details of the use of the compounds of this invention in NMR diagnostics will be along the lines of the use of other nitroxy compounds in the prior art except, of course, the advantageous properties of the compounds of this invention will be considered (see for example R. C. Brasch, T. N. Tozer, D. A. London: Radiology 1983, 147:773).

Herein, the term "nitroxyl" is used interchangeably with "nitroxide".

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2,2,5,5-Tetramethylpyrrolidine-1-oxyl-3-carboxylic Acid
[2-Hydroxy-2-(2,2-dimethyl-1,3-dioxolan-4-yl)ethyl]amide Under agitation, cooling, and covering with argon, 8.053 g (79.58 mmol) of triethylamine is added to a solution of 14.82 g (79.58 mmol) of 2,2,5,5-tetramethyl-pyrrolidine-1-oxyl-3-carboxylic acid in 200 ml of absolute tetrahydrofuran. After cooling to −5° C., 8.638 g (79.59 mmol) of chloroformic acid ethyl ester in 10 ml of absolute tetrahydrofuran is added dropwise in 45 minutes under agitation. The mixture is stirred for 30 minutes at −5° C. Then, 12.83 g (79.59 mmol) of 2-amino-1-(2,2-dimethyl-1,3-dioxolan-4-yl)ethanol is added in incremental portions. After 30 minutes, cooling is discontinued and the mixture is stirred for 3 hours at room temperature. The mixture is then diluted with 200 ml of absolute ether, suctioned off from the solid matter, which latter is washed with absolute ether. The organic solution is concentrated to dryness under vacuum. The residue is taken up in dichloromethane, washed with semisaturated sodium bicarbonate solution, dried over sodium sulfate, and concentrated to dryness under vacuum. The remaining yellow oil is crystallized after addition of diethyl ether. After recrystallization from ethyl acetate, the 2,2,5,5-tetramethyl-pyrrolidine-1-oxyl-3-carboxylic acid [2-hydroxy-2-(2,2-dimethyl-1,3-dioxolan-4-yl)ethyl]amide melts at 144° C., thus obtaining 14.79 g (56.4% of theory) of the compound. From the bicarbonate solution, 4.0 g of starting acid is recovered.

EXAMPLE 2

2,2,5,5-Tetramethylpyrrolidine-1-oxyl-3-carboxylic Acid (2,3,4-Trihydroxybutyl)amide 13.9 g (42.46 mmol) of 2,2,5,5-tetramethylpyrrolidine-1-oxyl-3-carboxylic acid [2-hydroxy-2-(2,2-dimethyl-1,3-dioxolan-4-yl)ethyl]amide is suspended in 150 ml of water containing 0.1 ml (3.6 mmol) of concentrated sulfuric acid. Under agitation, the mixture is heated to 40°–50° C. for 3 hours. The solution is cooled and the sulfuric acid neutralized with ion exchanger "Amberlite" IRA 410 OH⁻ form. The exchanger is filtered off and washed with water. The combined solutions are concentrated to dryness under vacuum. 2,2,5,5-Tetramethylpyrrolidine-1-oxyl-3-carboxy-(2,3,4-trihydroxybutyl)amide is crystallized from ethanol, thus obtaining 10.97 g (89.3% of theory) of yellow crystals, mp 172° C. Recrystallization from water yields yellow needles having a melting point of 189°–191° C.

EXAMPLE 3

2,2,5,5-Tetramethylpyrrolidine-1-oxyl-3-carboxylic Acid [N-(2,3,4,5,6-Pentahydroxyhexyl)-N-methyl]amide Under agitation, cooling, and covering with argon, 12.05 g (119 mmol) of triethylamine is added to a solution of 19.93 g (107 mmol) of 2,2,5,5-tetramethylpyrrolidine-1-oxyl-3-carboxylic acid in 300 of dimethylformamide. After cooling to −10° C., 12.92 g (119 mmol) of the ethyl ester of chloroformic acid in 30 ml of absolute tetrahydrofuran is added as a solution within 30 minutes to the mixture. After 10 minutes, 10.89 g (107 mmol) of N-methylglucamine is added in incremental portions. The mixture is stirred for 2 hours at 0° C., then cooling is discontinued and the mixture is agitated overnight at room temperature. The mixture is filtered off from the solid matter, which latter is washed with dimethylformamide and absolute tetrahydrofuran. The combined solutions are concentrated under vacuum, then finally with an oil pump. The residue is taken up in absolute tetrahydrofuran and decanted with diethyl ether. The thus-precipitated oil is dissolved in water and obtained in ion-free form by treatment with the ion exchanger "Amberlite" IR 120 H⁰ form and IRA 410 OH⁰ form. The yellow solution is concentrated to dryness under vacuum. The remaining syrup is stored under vacuum over diphosphoric pentoxide since it is strongly hygroscopic. Yield: 24.8 g (63.8% of theory) of 2,2,5,5-tetramethylpyrrolidine-1-oxyl-3-carboxylic acid [N-(2,3,4,5,6-pentahydroxyhexyl)-N-methyl]-amide as a yellow-orange syrup.

| $C_{16}H_{31}N_2O_7$ mol. wt. 363.43 | | | |
|---|---|---|---|
| Calculated: | 52.88 C | 8.60 H | 7.71 N |
| Found: | 52.61 C | 8.78 H | 7.59 N |

EXAMPLE 4

2,2,5,5-Tetramethylpyrrolidine-1-oxyl-3-carboxylic Acid (2,3-Dihydroxypropyl)amide Under agitation, cooling, and covering with argon, 8.13 g (80.3 mmol) of triethylamine is added to a solution of 13.61 g (73.1 mmol) of 2,2,5,5-tetramethylpyrrolidine-1-oxyl-3-carboxylic acid in 150 ml of dichloromethane. After cooling to −10° C., 8.72 g (80.3 mmol) of the ethyl ester of chloroformic acid in 10 ml of dichloromethane is added dropwise thereto, and after 20 minutes of agitation at −5° C., 6.66 g (73.1 mmol) of 2,3-dihydroxypropylamine in 40 ml of dimethylacetamide is added dropwise to the mixture. Cooling is discontinued, and the mixture is stirred for one hour, suctioned off from the solid matter, washed with absolute tetrahydrofuran, and concentrated to dryness under vacuum, and finally with an oil pump. The residue is extracted with absolute ether, dissolved in water, and obtained in ion-free form by treatment with ion exchanger "Amberlite" IR 120 H⁺ form and IRA 140 OH⁻ form. The yellow solution is concentrated to dryness under vacuum, thus producing 12.4 g (65.5% of theory) of 2,2,5,5-tetramethylpyrrolidine-1-oxyl-3-carboxylic acid (2,3-dihydroxypropyl)amide as a yellow-orange syrup.

| $C_{12}H_{23}N_2O_4$ MW 259.33 | | | |
|---|---|---|---|
| Calculated: | 55.58 C | 8.94 H | 10.80 N |
| Found: | 55.33 C | 9.19 H | 10.62 N |

EXAMPLE 5

2,2,5,5-Tetramethylpyrrolidine-1-oxyl-3-carboxylic Acid Bis(2-hydroxyethyl)amide Under agitation, cooling, and covering with argon, 7.69 g (76.0 mmol) of triethylamine is added to a solution of 12.91 g (69.32 mmol) of 2,2,5,5-tetramethylpyrrolidine-1-oxyl-3-carboxylic acid in 150 ml of absolute tetrahydrofuran. After cooling to −10° C., 8.25 g (76.0 mmol) of chloroformic acid ethyl ester in 10 ml of absolute tetrahydrofuran is added dropwise to the reaction mixture, and after 20 minutes of stirring at −5° C., 7.2 g (69.32 mmol) of diethanolamine in 40 ml of dioxane is added dropwise. The cooling is discontinued and the mixture is stirred for one hour. Then the mixture is diluted with 200 ml of absolute ether, suctioned off from the solid matter, washed with ether, and concentrated under vacuum. The residue is taken up in water and obtained in ion-free form by treatment with ion exchanger "Amberlite" IR 120 H⁺ form and IRA 410 OH⁻ form. the yellow, neutral solution is concentrated to dryness under vacuum, thus obtaining 11.64 g (61.4% of theory) of 2,2,5,5-tetramethylpyrrolidine-1-oxyl-3-carboxylic acid bis(2-hydroxyethyl)amide as a yellow-orange syrup.

| $C_{13}H_{25}N_2O_4$ MW 273.36 | | | |
|---|---|---|---|
| Calculated: | 57.12 C | 9.22 H | 10.25 N |
| Found: | 57.01 C | 9.38 H | 10.10 N |

EXAMPLE 6

2,2,5,5-Tetramethylpyrrolidine-1-oxyl-3-carboxylic Acid (1,3-Dihydroxyprop-2-yl)amide Under agitation and covering with argon, 6.65 g (61.27 mmol) of chloroformic acid ethyl ester in 10 ml of tetrahydrofuran is added dropwise at −5° C. to a solution of 11.41 g (61.27 mmol) of 2,2,5,5-tetramethylpyrrolidine-1-oxyl-3-carboxylic acid and 6.20 g (61.27 mmol) of triethylamine in 200 ml of absolute tetrahydrofuran. After 30 minutes, 5.59 g (61.3 mmol) of powdered 2-amino-1,3-propanediol is added in incremental portions. The cooling bath is removed and the mixture is stirred for another 5 hours. Then the mixture is diluted with 200 ml of absolute diethyl ether, suctioned off from the solid matter, washed with ether, and concentrated under vacuum. The residue is taken up in water and obtained in ion-free form by treatment with ion exchanger "Amerlite" IR 120 H⁺ form and IRA 410 OH⁻ form. The neutral, yellow solution is concentrated to dryness under vacuum, thus producing 10.1 g (64.4% of theory) of 2,2,5,5-tetramethylpyrrolidine-1-oxyl-3-carboxylic acid (1,3-dihydroxyprop-2-yl)-amide as a dark-yellow syrup.

| $C_{12}H_{23}N_2O_4$ (259.33) | | | |
|---|---|---|---|
| Calculated: | 55.58 C | 8.94 H | 10.80 N |
| Found: | 55.37 C | 9.19 H | 10.64 N |

EXAMPLE 7

2,2,5,5-Tetramethyl-3-pyrroline-3-carboxylic Acid (2,2-Dimethyl-1,3-dioxolan-4-ylmethyl)amide Under agitation, cooling between −5° and 0° C., and covering with argon, 68.94 g (175 mmol) of 3,5-dibromo-2,2,6,6-tetramethylpiperidin-4-one hydrobromide is added in portions to a solution of 22.93 g (175 mmol) of (2,2-dimethyl-1,3-dioxolan-4-yl)methylamine and 58.9 g (525 mmol) of potassium tert-butylate in 700 ml of isopropanol. A white paste is thus obtained which is stirred for one hour without cooling, suctioned off from the solid matter, and concentrated to dryness under vacuum. The residue is distributed between dichloromethane and water. The organic phase is dried over sodium sulfate and concentrated to dryness under vacuum. The residue is crystallized. After recrystallization from pentane, 30.1 g (60.9% of theory) of 2,2,5,5-tetramethyl-3-pyrroline-3-carboxylic acid (2,2-dimethyl-1,3-dioxolan-4-ylmethyl)amide is obtained, mp 55°–57° C.

| $C_{15}H_{26}N_2O_3$ (282.40) | | | |
|---|---|---|---|
| Calculated: | 63.35 C | 9.92 H | 9.82 N |
| Found: | 63.11 C | 9.72 H | 9.99 N |

EXAMPLE 8

2,2,5,5-Tetramethyl-3-pyrroline-1-oxyl-3-carboxylic Acid (2,2-Dimethyl-1,3-dioxolan-4-ylmethyl)amide A solution is prepared from 200 ml of absolute diethyl ether and 15.88 g (56.23 mmol) of 2,2,5,5-tetramethyl-3-pyrroline-3-carboxylic acid (2,2-dimethyl-1,3-dioxolan-4-ylmethyl)amide, cooled to −5° C., and combined in portions under agitation with a solution of 23.92 g (112.4 mmol) of 3-chloroperbenzoic acid, 80%, in 150 ml of absolute ether. The cooling bath is removed, the mixture is stirred for another 2 hours, stirred into 200 ml of soda solution containing 29 g of sodium carbonate decahydrate, and the product is taken up in diethyl ether. The ether solution is dried over sodium sulfate and concentrated to dryness under vacuum, thus obtaining 16.46 g (98.4% of theory) of 2,2,5,5-tetramethyl-3-pyrroline-1-oxyl-3-carboxylic acid (2,2-dimethyl-1,3-dioxolan-4-ylmethyl)amide as an orange-colored syrup.

| $C_{15}H_{25}N_2O_4$ (297.38) | | | |
|---|---|---|---|
| Calculated: | 60.59 C | 8.47 H | 9.42 N |
| Found: | 60.33 C | 8.68 H | 9.30 N |

EXAMPLE 9

2,2,5,5-Tetramethyl-3-pyrroline-1-oxyl-3-carboxylic Acid (2,3-Dihydroxypropyl)amide A suspension is prepared from 14.2 g (47.8 mmol) of 2,2,5,5-tetramethyl-3-pyrroline-1-oxyl-3-carboxylic acid (2,2-dimethyl-1,3-dioxolan-4-ylmethyl)amide in 100 ml of distilled water containing 0.1 ml (3.6 mmol) of concentrated sulfuric acid, and the suspension is stirred for 3 hours at 50° C. After cooling, the mixture is neutralized with ion exchanger "Amberlite" IRA 410 OH⁻ form. The resin is washed with water and the combined solutions are concentrated under vacuum. The remainder is dried with an oil pump at room temperature, thus producing 10.48 g (85.3% of theory) of crystalline 2,2,5,5-tetramethyl-3-pyrroline-1-oxyl-3-carboxylic acid (2,3-dihydroxypropyl)amide having a melting point of 131°–133° C.

| $C_{12}H_{21}N_2O_4$ | (257.31) | | |
|---|---|---|---|
| Calculated: | 56.02 C | 8.23 H | 10.89 N |
| Found: | 55.87 C | 8.39 H | 10.74 N |

EXAMPLE 10

2,2,5,5-Tetramethyl-3-pyrroline-3-carboxylic Acid [N-(2,2-Dimethyl-1,3-dioxolan-4-ylmethyl)-N-methyl]amide Anologously to Example 7, the following compounds are reacted: 68.94 g (175 mmol) of 3,5-dibromo-2,2,6,6-tetramethylpiperidin-4-one hydrobromide, 58 g (525 mmol) of potassium tert-butylate, and 25.41 g (115 mmol) of N-methyl-N-(2,2-dimethyl-1,3-dioxolan-4-ylmethyl)amine in 600 ml of isopropanol.

Yield: 39.43 g (76% of theory) of 2,2,5,5-tetramethyl-3-pyrroline-3-carboxylic acid [N-(2,2-dimethyl-1,3-dioxolan-4-ylmethyl)-N-methyl]amide as an orange-colored syrup.

| $C_{10}H_{28}N_2O_3$ | (296.41) | | |
|---|---|---|---|
| Calculated: | 64.84 C | 9.52 H | 9.45 N |
| Found: | 64.59 C | 9.73 H | 9.27 N |

EXAMPLE 11

2,2,5,5-Tetramethyl-3-pyrroline-1-oxyl-3-carboxylic Acid [N-(2,2-Dimethyl-1,3-dioxolan-4-ylmethyl)-N-methyl]amide Analogously to Example 8, the following compounds are reacted:

14.97 g (50.50 mmol) of 2,2,5,5-tetramethyl-3-pyrroline-3-carboxylic acid N-[(2,2-dimethyl-1,3-dioxolan-4-yl)methyl]-N-methylamide with 22.0 g (101 mmol) of 3-chloro-perbenzoic acid, 80%, in 300 ml of absolute diethyl ether, thus obtaining 13.12 g (83.5% of theory) of 2,2,5,5-tetramethyl-3-pyrroline-1-oxyl-3-carboxylic acid [N-(2,2-dimethyl-1,3-dioxolan-4-ylmethyl)-N-methyl]amide, exhibiting a melting point of 69°–71° C. after crystallization from ethyl acetate.

| $C_{16}H_{28}N_2O_3$ | (296.41) | | |
|---|---|---|---|
| Calculated: | 61.51 C | 9.03 H | 8.97 N |
| Found: | 61.80 C | 8.98 H | 8.87 N |

EXAMPLE 12

2,2,5,5-Tetramethyl-3-pyrroline-1-oxyl-3-carboxylic acid N-(2,3-dihydroxypropyl)-N-methylamide In analogy to Example 9, 11.49 g (36.9 mmol) of 2,2,5,5-tetramethyl-3-pyrroline-1-oxyl-3-carboxylic acid [N-(2,2-dimethyl-1,3-dioxolan-4-ylmethyl)-N-methyl]amide is saponified in 100 ml of distilled water containing 0.05 ml (1.8 mmol) of concentrated sulfuric acid, thus producing 9.18 g (91.7% of theory) of 2,2,5,5-tetramethyl-3-pyrroline-1-oxyl-3-carboxylic acid N-(2,3-dihydroxypropyl)-N-methylamide as an orange-colored syrup.

| $C_{13}H_{23}N_2O_4$ | (271.34) | | |
|---|---|---|---|
| Calculated: | 57.55 C | 8.54 H | 10.32 N |
| Found: | 57.33 C | 8.75 H | 10.18 N |

EXAMPLE 13

2,2,5,5-Tetramethylpyrrolidine-3-carboxylic Acid N-[(2,2-Dimethyl-1,3-dioxolan-4-ylmethyl)-N-methyl]amide 2 g of Raney nickel B 115 Z is added to a solution of 22.58 g (76.18 mmol) of 2,2,5,5-tetramethyl-3-pyrroline-3-carboxylic acid N-(2,2-dimethyl-1,3-dioxolan-4-ylmethyl)amide in 400 ml of methanol and hydrogenation is carried out under an initial pressure of 180 bar. Exactly one mole of hydrogen is absorbed. The product is suctioned off from the catalyst, the solution is treated with carbon and concentrated to dryness under vacuum, thus obtaining 21.0 g (92.4% of theory) of 2,2,5,5-tetramethylpyrrolidine-3-carboxylic acid [N-(2,2-dimethyl-1,3-dioxolan-4-ylmethyl)-N-methyl]amide as a pale-yellow oil.

| $C_{16}H_{30}N_2O_3$ | (298.43) | | |
|---|---|---|---|
| Calculated: | 64.40 C | 10.13 H | 9.39 N |
| Found: | 64.66 C | 10.21 H | 9.57 N |

EXAMPLE 14

2,2,5,5-Tetramethylpyrrolidine-1-oxyl-3-carboxylic Acid [N-(2,2-Dimethyl-1,3-dioxolan-4-ylmethyl)-N-methyl]amide Analogously to Example 8, the following compounds are reacted:

20.78 g (69.63 mmol) of 2,2,5,5-tetramethylpyrrolidine-3-carboxylic acid N-[(2,2-dimethyl-1,3-dioxolan-4yl-methyl)-N-methyl]amide with 30 g (140 mmol) of 3-chloroperbenzoic acid, 80%, in 400 ml of absolute diethyl ether. Yield: 17.52 g (80.3% of theory) of 2,2,5,5-tetramethylpyrrolidine-1-oxyl-3-carboxylic acid [N-(2,2-dimethyl-1,3-dioxolan-4-ylmethyl)-N-methyl]amide as an orange-colored syrup.

| $C_{16}H_{29}N_2O_4$ | (313.42) | | |
|---|---|---|---|
| Calculated: | 61.32 C | 9.33 H | 8.94 N |
| Found: | 61.61 C | 9.40 H | 8.83 N |

EXAMPLE 15

2,2,5,5-Tetramethylpyrrolidine-1-oxyl-3-carboxylic Acid N-(2,3-Dihydroxypropyl)-N-methylamide Analogously to Example 9, 16.60 g (53 mmol) of 2,2,5,5-tetramethylpyrrolidine-1-oxyl-3-carboxylic acid [N-(2,2-dimethyl-1,3-dioxolan-4-ylmethyl)-N-methyl]amide is saponified in 150 ml of distilled water wherein is dissolved 0.05 ml (1.8 mmol) of concentrated sulfuric acid. Yield: 13.28 g (91.7% of theory) of 2,2,5,5-tetramethylpyrrolidine-1-oxyl-3-carboxylic acid N-(2,3-dihydroxpropyl)-N-methylamide as an orange-colored syrup.

| $C_{13}H_{25}N_2O_4$ | (273.36) | | |
|---|---|---|---|
| Calculated: | 57.12 C | 9.22 H | 10.25 N |
| Found: | 56.86 C | 9.39 H | 10.06 N |

EXAMPLE 16

2,2,5,5-Tetramethyl-3-pyrroline-3-carboxylic Acid [2-Hydroxy-2-(2,2-dimethyl-1,3-dioxolan-4-yl)ethyl]amide In analogy to Example 7, the following compounds are reacted:

51.22 g (130 mmol) of 3,5-dibromo-2,2,6,6-tetramethylpiperidin-4-one hydrobromide, 45.05 g (390 mmol) of potassium tert-butylate, and 20.96 g (130 mmol) of 2-amino-1-(2,2-dimethyl-1,3-dioxolan-4-yl)ethanol in 500 ml of isopropanol, thus obtaining 22.93 g (56.5% of theory) of 2,2,5,5-tetramethyl-3-pyrroline-3-carboxylic acid [2-hydroxy-2-(2,2-dimethyl-1,3-dioxolan-4-yl)ethyl]amide which, crystallized from diethyl ether/pentane, has a melting point of 99°–101° C.

| $C_{16}H_{28}N_2O_4$ | (312.41) | | |
|---|---|---|---|
| Calculated: | 61.51 C | 9.03 H | 8.97 N |
| Found: | 61.57 C | 9.33 H | 8.90 N |

EXAMPLE 17

2,2,5,5-Tetramethyl-3-pyrroline-1-oxyl-3-carboxylic Acid [2-Hydroxy-2-(2,2-dimethyl-1,3-dioxolan-4-yl)ethyl]amide In analogy to Example 8, the following compounds are reacted:

2.81 g (9 mmol) of 2,2,5,5-tetramethyl-3-pyrroline-3-carboxylic acid [2-hydroxy-2-(2,2-dimethyl-1,3-dioxolan-4-yl)ethyl]amide with 4.72 g (18 mmol) of 3-chloroperbenzoic acid in 100 ml of absolute diethyl ether, thus obtaining 2.43 g (83.5% of theory) of 2,2,5,5-tetramethyl-3-pyrroline-1-oxyl-3-carboxylic acid [2-hydroxy-2-(2,2-dimethyl-1,3-dioxolan-4-yl)ethyl]amide, mp 104°–105° C.

| $C_{16}H_{27}N_2O_5$ | (327.40) | | |
|---|---|---|---|
| Calculated: | 58.70 C | 8.31 H | 24.43 N |
| Found: | 58.46 C | 9.57 H | 24.28 N |

EXAMPLE 18

2,2,5,5-Tetramethyl-3-pyrroline-1-oxyl-3-carboxylic Acid [2-Hydroxy-2-(2,2-dimethyl-1,3-dioxolan-4-yl)ethyl]amide 15.98 g (51.15 mmol) of 2,2,5,5-tetramethyl-3-pyrroline-3-carboxylic acid [2-hydroxy-2-(2,2-dimethyl-1,3-dioxolan-4-yl)ethyl]amide is dissolved in 100 ml of distilled water and combined with 500 mg (1.34 mmol) of "Titriplex" III, 500 mg (1.52 mmol) of sodium tungstate dihydrate, as well as 10 ml (88.2 mmol) of 30% hydrogen peroxide. The mixture is stirred for 5 days at room temperature in a dark flask, acidified with citric acid to pH 3, and the product is extracted with dichloromethane. The organic solution is washed with water, dried over sodium sulfate, and concentrated to dryness under vacuum. The orange-colored oil is taken up in diethyl ether and made to crystallize, thus obtaining 12.79 g (76.4% of theory) of 2,2,5,5-tetramethyl-3-pyrroline-1-oxyl-3-carboxylic acid [2-hydroxy-2-(2,2-dimethyl-1,3-dioxolan-4-yl)ethyl]amide, mp 105°–106° C.

EXAMPLE 19

2,2,5,5-Tetramethyl-3-pyrroline-1-oxyl-3-carboxylic Acid (2,3,4-Trihydroxybutyl)amide Analogously to Example 9, 15.56 g (47.53 mmol) of 2,2,5,5-tetramethyl-3-pyrroline-1-oxyl-3-carboxylic acid [2-hydroxy-2-(2,2-dimethyl-1,3-dioxolan-4-yl)ethyl]amide is saponified in 200 ml of distilled water containing 0.15 ml (5.4 mmol) of concentrated sulfuric acid. The product is crystallized from water, thus obtaining 12.87 g (94.2% of theory) of 2,2,5,5-tetramethyl-3-pyrroline-1-oxyl-3-carboxylic acid (2,3,4-trihydroxybutyl)amide, mp 183°–185° C.

| $C_{13}H_{23}N_2O_5$ | | (287.34) | |
|---|---|---|---|
| Calculated: | 54.34 C | 8.07 H | 9.75 N |
| Found: | 54.21 C | 8.28 H | 9.58 N |

EXAMPLE 20

2,2,5,5-Tetramethyl-3-pyrroline-3-carboxylic Acid (5-Hydroxy-2,2-dimethyl-1,3-dioxepan-6-yl)-amide Analogously to Example 7, 78.79 g (200 mmol) of 3,5-dibromo-2,2,6,6-tetramethylpiperidin-4-one hydrobromide, 69.34 g of potassium tert-butylate, and 35.47 g (220 mmol) of 6-amino-2,2-dimethyl-1,3-dioxepan-5-ol are reacted in 800 ml of isopropanol and then extracted with dichloromethane. Yield: 37.66 g (60.3% of theory) of 2,2,5,5-tetramethyl-3-pyrroline-3-carboxylic acid (5-hydroxy-2,2-dimethyl-1,3-dioxepan-6-yl)amide which, crystallized from diethyl ether/hexane, shows a melting point of 125°–127° C.

| $C_{16}H_{28}N_2O_4$ | | (312.41) | |
|---|---|---|---|
| Calculated: | 61.51 C | 9.03 H | 8.97 N |
| Found: | 61.32 C | 9.20 H | 8.83 N |

EXAMPLE 21

2,2,5,5-Tetramethyl-3-pyrroline-1-oxyl-3-carboxylic Acid (5-Hydroxy-2,2-dimethyl-1,3-dioxepan-6-yl)amide Analogously to Example 8, the following compounds are reacted:

13.0 g (41.61 mmol) of 2,2,5,5-tetramethyl-3-pyrroline-3-carboxylic acid (5-hydroxy-2,2-dimethyl-1,3-dioxepan-6-yl)amide with 19.15 g (90.0 mmol) of 3-chloroperbenzoic acid, 80%, in 130 ml of dichloromethane, thus obtaining 11.23 g (82.5% of theory) of 2,2,5,5-tetramethyl-3-pyrroline-1-oxyl-3-carboxylic acid (5-hydroxy-2,2-dimethyl1,3-dioxepan-6-yl)amide which, crystallized from diethyl ether/hexane, shows a melting point of 132°–133° C.

| $C_{16}H_{27}N_2O_5$ | | (327.40) | |
|---|---|---|---|
| Calculated: | 58.70 C | 8.31 H | 8.56 N |
| Found: | 58.04 C | 8.59 H | 8.34 N |

EXAMPLE 22

2,2,5,5-Tetramethyl-3-pyrroline-1-oxyl-3-carboxylic Acid (1,3,4-Trihydroxybut-2-yl)amide Analogously to Example 9, 12.53 g (38.27 mmol) of 2,2,5,5-tetramethyl-3-pyrroline-1-oxyl-3-carboxylic acid (5-hydroxy-2,2-dimethyl-1,3-dioxepan-6-yl)amide is saponified in 100 ml of distilled water containing 0.1 ml (3.6 mmol) of concentrated sulfuric acid. The product is crystallized from the concentrated aqueous solution, thus obtaining 9.60 g (87.3% of theory) of 2,2,5,5-tetramethyl-3-pyrroline-1-oxyl-3-carboxylic acid (1,3,4-trihydroxybut-2-yl)amide, mp 75°–77° C.

| $C_{13}H_{23}N_2O_5$ | | (287.34) | |
|---|---|---|---|
| Calculated: | 54.34 C | 8.07 H | 9.75 N |
| Found: | 54.36 C | 8.32 H | 9.60 N |

EXAMPLE 23

2,2,5,5-Tetramethylpyrrolidine-1-oxyl-3-carboxylic Acid (5-Hydroxy-2,2-dimethyl-1,3-dioxepan-6-yl)amide In analogy to Example 4, the following compounds are reacted:

24.23 g (130.11 mmol) of 2,2,5,5-tetramethyl-pyrrolidine-1-oxyl-3-carboxylic acid, 13.59 g (133.0 mmol) of triethylamine, 14.87 g (133.0 mmol) of chloroformic acid ethyl ester, 21.44 g (133 mmol) of 6-amino-2,2-dimethyl-1,3-dioxepan-5-ol in 350 ml of absolute tetrahydrofuran, thus obtaining 24.83 g (56.7% of theory) of 2,2,5,5-tetramethylpyrrolidine-1-oxyl-3-carboxylic acid (5-hydroxy-2,2-dimethyl-1,3-dioxepan-6-yl)amide which, crystallized from diethyl ether, has a melting point of 190°–191° C.

| $C_{16}H_{29}N_2O_5$ | | (329.42) | |
|---|---|---|---|
| Calculated: | 58.34 C | 8.87 H | 8.50 N |
| Found: | 58.20 C | 8.99 H | 8.39 N |

EXAMPLE 24

2,2,5,5-Tetramethylpyrrolidine-1-oxyl-3-carboxylic Acid (1,3,4-Trihydroxybut-2-yl)amide In analogy to Example 9, 6.0 g (18.21 mmol) of 2,2,5,5-tetramethylpyrrolidine-1-oxyl-3-carboxylic acid (5-hydroxy-2,2-dimethyl-1,3-dioxepan-6-yl)amide is saponified in 100 ml of distilled water containing 0.05 ml (1.8 mmol) of concentrated sulfuric acid, thus obtaining 4.83 g (91.7% of theory) of 2,2,5,5-tetramethylpyrrolidine-1-oxyl-3-carboxylic acid (1,3,4-trihydroxybut-2-yl)amide as an orange-colored syrup.

| $C_{13}H_{25}N_2O_5$ | | (289.35) | |
|---|---|---|---|
| Calculated: | 53.96 C | 8.71 H | 9.68 N |
| Found: | 53.98 C | 8.91 H | 9.57 N |

EXAMPLE 25

2,2,5,5-Tetramethyl-3-pyrroline-1-oxyl-3-carboxylic Acid [N-(2,3,4,5,6-Pentahydroxyhexyl)-N-methyl]amide Analogously to Example 4, the following compounds are reacted:

12.90 g (70 mmol) of 2,2,5,5-tetramethyl-3-pyrroline-1-oxyl-3-carboxylic acid with 7.51 g (73.5 mmol) of triethylamine, 8.22 g (73.5 mmol) of chloroformic acid ethyl ester in 150 ml of absolute tetrahydrofuran to obtain the anhydride which is suctioned off by way of a porous glass plate and combined with 14.35 g (73.5 mmol) of N-methylglucamine in 80 ml of absolute pyridine. The mixture is agitated overnight, concentrated under vacuum, residues of pyridine are removed by codistillation with ethanol, and the product is purified by chromatography on 800 g of silica gel with ethyl acetate/ethanol 2:1 as the eluent, thus producing 16.11 g (63.7% of theory) of 2,2,5,5-tetramethyl-3-pyrroline-1-oxyl-3-carboxylic acid [N-(2,3,4,5,6-pentahydroxyhexyl)-N-methyl]amide as an orange syrup.

| $C_{16}H_{29}N_2O_7$ | (361.42) | | |
|---|---|---|---|
| Calculated: | 53.17 C | 8.09 H | 7.75 N |
| Found: | 52.93 C | 8.22 H | 7.58 N |

EXAMPLE 26

2,2,5,5-Tetramethyl-3-pyrroline-1-oxyl-3-carboxylic Acid (1,3-Dihydroxyprop-2-yl)amide The following compounds are reacted in analogy to Example 4:

5.50 g (29.86 mmol) of 2,2,5,5-tetramethyl-3-pyrroline-1-oxyl-3-carboxylic acid, 3.27 g (32 mmol) of triethylamine, 3.58 g (32 mmol) of chloroformic acid ethyl ester, and 2.92 g (32 mmol) of 2-amino-1,3-propanediol in 100 ml of absolute tetrahydrofuran, thus obtaining 5.27 g (68.6% of theory) of 2,2,5,5-tetramethyl-3-pyrroline-1-oxyl-3-carboxylic acid (1,3-dihydroxyprop-2-yl)amide which crystallizes upon standing and has a melting point of 151°–153° C.

| $C_{12}H_{21}N_2O_4$ | (257.31) | | |
|---|---|---|---|
| Calculated: | 56.01 C | 8.23 H | 10.89 N |
| Found: | 55.80 C | 8.49 H | 10.71 N |

EXAMPLE 27

2,2,5,5-Tetramethylpyrrolidine-1-oxyl-3-carboxylic Acid N-(1,3-Dihydroxyprop-2-yl)amide A mixture of 1.00 g (5 mmol) of 2,2,5,5-tetramethylpyrrolidine-1-oxyl-3-carboxylic acid methyl ester and 0.68 g (7.5 mmol) of 2-amino-1,3-propanediol is heated for 6 hours under argon to 120° C. After cooling, the mixture is taken up in distilled water, extracted with diethyl ether, and excess amine is bound by treatment with ion exchanger "Amberlite" IR 120 H+ form. The exchanger is removed by filtration, washed with water, and the combined aqueous phases are concentrated to dryness under vacuum, thus obtaining 790 mg (60.8% of theory) of 2,2,5,5-tetramethylpyrrolidine-1-oxyl-3-carboxylic acid (1,3-dihydroxyprop-2-yl)amide as an orange-colored oil.

| $C_{12}H_{23}N_2O_4$ | (259.33) | | |
|---|---|---|---|
| Calculated: | 55.58 C | 8.94 H | 10.80 N |
| Found: | 55.29 C | 9.22 H | 10.72 N |

EXAMPLE 28

2,2,5,5-Tetramethyl-3-pyrroline-1-oxyl-3-carboxylic Acid (5-Hydroxy-2,2-dimethyl-1,3-dioxepan-6-yl)amide Under agitation of 0° C., a solution of 2.563 g (10 mmol) of mixed anhydride from 2,2,5,5-tetramethyl-3-pyrroline-1-oxyl-3-carboxylic acid and chloroformic acid ethyl ester in 20 ml of dichloromethane is added dropwise to a solution of 1.61 g (10 mmol) of 6-amino-2,2-dimethyl-1,3-dioxepan-5-ol in 100 ml of dichloromethane. The mixture is stirred for another 60 minutes, the solution is washed with saturated sodium bicarbonate solution, the organic phase is separated, dried over sodium sulfate, and concentrated under vacuum. The residue is crystallized from diethyl ether/hexane, thus obtaining 2.27 g (69.3% of theory) of 2,2,5,5-tetramethyl-3-pyrroline-1-oxyl-3-carboxylic acid (5-hydroxy-2,2-dimethyl-1,3-dioxepan-6-yl)amide, mp 132°–133° C.

EXAMPLE 29

Succinic Acid [N-[2-Hydroxy-2-(2,2-dimethyl-1,3-dioxolan-4-yl)ethyl]-N'-(2,2,6,6-tetramethyl-1-oxylpiperidin-4-yl)] Diamide Under agitation, cooling, and under nitrogen purging, 1.01 g (=10 mmol) of triethylamine is added to a solution of 2.71 g (=10 mmol) of succinic acid (2,2,6,6-tetramethyl-1-oxido-4-piperidyl) monoamide in 200 ml of absolute tetrahydrofuran. The mixture is cooled to −5° C. and, within 20 minutes, 1.09 g (=10 mmol) of methyl ester of chloroformic acid, dissolved in 10 ml of absolute tetrahydrofuran, is added dropwise under stirring to the reaction mixture. The latter is stirred for 30 minutes at −5° C. Then, 1.61 g (=10 mmol) of 2-amino-1-(2,2-dimethyl-1,3-dioxolan-4-yl)-ethanol is added thereto in incremental portions. After 30 minutes, cooling is discontinued and the mixture is agitated for 3 hours at room temperature. Thereafter the mixture is diluted with 200 ml of absolute ether, suctioned off from the solid matter which latter is discarded after washing with absolute ether. The organic solution is concentrated to dryness under vacuum, the residue is taken up in dichloromethane, washed with a small amount of ice-cold, semisaturated sodium bicarbonate solution, and, after drying over sodium sulfate, the organic phase is again concentrated to dryness under vacuum, thus obtaining 2.6 g (=63% of theory) of an orange-colored syrup.

| $C_{20}H_{36}N_3O_6$ | (414.520) | | |
|---|---|---|---|
| Calculated: | 57.95 C | 8.75 H | 10.14 N |
| Found: | 57.86 C | 9.00 H | 10.20 N |

EXAMPLE 30

Succinic Acid
[N-(2,2,6,6-Tetramethyl-1-oxyl-piperidin-4-yl)-N'-(2,3,4-trihydroxybutyl)] Diamide A suspension is prepared from 50 ml of water containing 0.1 ml of concentrated sulfuric acid and 2.05 g (=5 mmol) of succinic acid [N-[2-hydroxy-2-(2,2-dimethyl-1,3-dioxolan-4-yl)ethyl]-N'-(2,2,6,6-tetramethyl-1-oxylpiperidin-4-yl)] diamide. Under agitation, the mixture is heated to 50° C. for 3 hours, then cooled to room temperature, and the solution is neutralized with ion exchanger "Amberlite" IRA 410 (OH⁻ form). The exchanger is removed by filtration and the solution concentrated to dryness under vacuum, thus obtaining 1.67 g (=90% of theory) of an orange-colored syrup.

| $C_{17}H_{32}N_3O_6$ | (374.456) | | |
|---|---|---|---|
| Calculated: | 54.53 C | 8.61 H | 11.22 N |
| Found: | 54.44 C | 8.80 H | 11.02 N |

EXAMPLE 31

2,2,6,6-Tetramethyl-1,2,5,6-tetrahydropyridine-1-oxyl-4-carboxylic Acid
[N-(2,3,4,5,6-Pentahydroxyhexyl)-N-methyl]amide Analogously to Example 4, the following compounds are reacted:

7.93 g (40 mmol) of 2,2,6,6-tetramethyl-1,2,5,6-tetrahydropyridine-1-oxyl-4-carboxylic acid with 4.3 g (42.5 mmol) of triethylamine, 4.61 g (42.5 mmol) of chloroformic acid ethyl ester in 100 ml of absolute tetrahydrofuran to obtain the mixed anhydride which is combined, by vacuum-filtering over a porous glass plate, with 8.3 g (42.5 mmol) of N-methylglucamine in 50 ml of absolute pyridine. The mixture is stirred overnight, concentrated under vacuum, residues of pyridine are removed by codistillation with ethanol, and the product is purified by chromatography on 500 g of silica gel with ethyl acetate/ethanol 2:1 as the eluent, thus obtaining 9.19 g (61.2% of theory) of 2,2,6,6-tetramethyl-1,2,5,6-tetrahydropyridine-1-oxyl-4-carboxylic acid [N-(2,3,4,5,6-pentahydroxyhexyl)-N-methyl]amide as an orange syrup.

| $C_{17}H_{31}N_2O_7$ | (375.45) | | |
|---|---|---|---|
| Calculated: | 54.39 C | 8.32 H | 7.46 N |
| Found: | 54.12 C | 8.51 H | 7.30 N |

EXAMPLE 32

(1-Oxyl-2,2,6,6-tetramethylpiperidin-4-yl)acetic Acid
[N-(2,3,4,5,6-Pentahydroxyhexyl)-N-methyl]amide Analogously to Example 4, the following compounds are reacted:

8.57 g (40 mmol) of (1-oxyl-2,2,6,6-tetramethylpiperidin-4-yl)acetic acid with 4.3 g (42.5 mmol) of triethylamine, 4.61 g (4.25 mmol) of chloroformic acid ethyl ester in 100 ml of absolute tetrahydrofuran to obtain the mixed anhydride which is combined, by suctioning through a porous glass plate, with 8.3 g (42.5 mmol) of N-methylglucamine in 50 ml of absolute pyridine. The mixture is worked up as described in Example 25, thus obtaining 9.36 g (59.8% of theory) of (1-oxyl-2,2,6,6-tetramethylpiperidin-4-yl)acetic acid [N-(2,3,4,5,6-pentahydroxyhexyl)-N-methyl]amide as an orange syrup.

| $C_{18}H_{35}N_2O_7$ | (391.49) | | |
|---|---|---|---|
| Calculated: | 55.23 C | 9.01 H | 7.16 N |
| Found: | 55.44 C | 9.18 H | 7.02 N |

EXAMPLE 33

Succinic Acid
(1-Oxyl-2,2,5,5-tetramethyl-pyrrolidin-3-yl) Monoamide

Under cooling, a solution of 6.20 g (62 mmol) of succinic anhydride in 65 ml of absolute tetrahydrofuran is added dropwise to a solution of 7.86 g (50 mmol) of 2,2,5,5-tetramethylpyrrolidine-1-oxyl-3-amine in 10 ml of pyridine. After agitation overnight, the solvent is removed under vacuum, the residue is stirred into 250 ml of water, and the solution is extracted with diethyl ether. The aqueous solution is concentrated under vacuum to 30 ml and cooled. The thus-separated solid matter is suctioned off and dried under vacuum, thus obtaining 9.62 g (74.8% of theory) of succinic acid (1-oxyl-2,2,5,5-tetramethylpyrrolidin-3-yl) monoamide.

| $C_{12}H_{21}N_2O_4$ | (257.31) | | |
|---|---|---|---|
| Calculated: | 56.02 C | 8.23 H | 10.89 N |
| Found: | 56.18 C | 8.22 H | 11.00 N |

EXAMPLE 34

Succinic Acid
[N-(1-Oxyl-2,2,5,5-tetramethylpyrrolidin-3-yl)-N'-methyl-N'-(2,3,4,5,6-pentahydroxyhexyl)] Diamide Analogously to Example 4, the following compounds are reacted:

10.29 g (40 mmol) of succinic acid (1-oxyl-2,2,5,5-tetramethylpyrrolidin-3-yl) monoamide with 4.3 g (42.5 mmol) of triethylamine and 4.61 g (42.5 mmol) of chloroformic acid ethyl ester in 100 ml of absolute tetrahydrofuran to obtain the anhydride which is combined by suctioning off via a porous glass plate with 8.3 g (42.5 mmol) of N-methylglucamine in 50 ml of absolute pyridine. The mixture is worked up as described in Example 25, thus producing 10.53 g (62.6% of theory) of succinic acid [N-(1-oxyl-2,2,5,5-tetramethylpyrrolidin-3-yl)-N'-methyl-N'-(2,3,4,5,6-pentahydroxyhexyl)] diamide as an orange-colored syrup.

| $C_{19}H_{36}N_2O_8$ | (420.51) | | |
|---|---|---|---|
| Calculated: | 54.27 C | 8.63 H | 6.66 N |
| Found: | 54.09 C | 8.47 H | 6.49 N |

EXAMPLE 35

Solution of
2,2,5,5-Tetramethyl-3-pyrroline-1-oxyl-3-carboxylic Acid 2,3-Dihydroxypropylamide Under heating, 258.317 g (=1 mol) of 2,2,5,5-tetramethyl-3-pyrroline-1-oxyl-3-carboxylic acid 2,3-dihydroxypropylamide is dissolved in 600 ml of water pro injectione. To this solution is added 1.2 g of tromethamine, filled with water pro injectione to 1,000 ml, and the sterile-filtered, neutral solution is dispensed into bottles.

Agents for NMR diagnostics.

EXAMPLE 36

Preparation of Liposomes Loaded with Nitroxyl Compounds

In accordance with the method described in Proc. Nat. Acad. Sci. USA 75:4194, a lipid mixture made up of 50 parts of egg phosphatidylchlorine and 50 parts of cholesterol is prepared as a dry composition. Of this, 500 mg is dissolved in 30 ml of peroxide-free diethyl ether and combined, in an ultrasonic bath, dropwise with 3 ml of a one-molar solution of 2,2,5,5-tetramethyl-pyrrolidine-1-oxyl-3-carboxylic acid (2,3-dihydroxypropyl)amide in water pro injectione. After this addition is completed, the ultrasonic treatment is continued for 5 minutes and then the mixture is concentrated in a rotational evaporator ("Rotavapor"). The thus-obtained microemulsion is diluted with physiological sodium chloride solution and at 0° C. freed repeatedly by centrifuging (20,000 g/20 minutes) of not encapsulated contrast media proportions. Then the liposomes are freeze-dried in a multivial. Administration is effected as a dispension of physiological sodium chloride solution, providing a good contrasting imaging of the liver and spleen upon intravenous injection in a dose of 2.4–5.0 ml/kg.

EXAMPLE 37

Preparation of a Solution of a Nitroxyl-Protein Conjugate 144.5 mg (=0.5 mmol) of 2,2,5,5-tetramethylpyrrolidine-1-oxyl-3-carboxylic acid (1,2,4-trihydroxybut-3-yl)amide is dissolved in 10 ml of dimethyl sulfoxide. The solution is cooled and, under agitation, combined dropwise with a solution of 57.6 mg (0.5 mmol) of N-hydroxysuccinimide in 2.0 ml of dimethyl sulfoxide, thereupon dropwise with a solution of 92.9 mg (0.45 mmol) of dicyclohexyl carbondiimide in 2.5 ml of dimethyl sulfoxide. After agitation overnight, the mixture is filtered and an adequate portion of the solution with the desired molar ratio is gradually added to a solution of IgG in 0.1-molar sodium phosphate/sodium chloride buffer (pH 8.0), IgG concentration: 2.6'3.4 mg/ml. The mixture is agitated for 2 hours at room temperature, the protein fraction is separated by way of a Bio-Gel P 30 column, and dialyzed in succession at 4° C. for 24 hours against 800 ml of 0.9% sodium chloride−0.02% sodium azide solution and against 800 ml of a 0.1-molar sodium citrate buffer (pH 5.0). A stable dry preparation is obtained by freezer-drying and storage at low temperature which, when required, is dissolved in water pro injectione. The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various charges and modifications of the invention to adapt it to various usages and conditions.

What is claimed is:

1. A method of obtaining an MRI image of a patient comprising administering to the patient an amount effective as a contrast agent of a compound of the formula

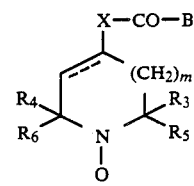

wherein

B is a pharmacologically acceptable protein, sugar, or lipid residue, that selectively binds to a biological molecule, or

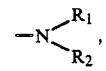

==== is a single or double bond,

X is —$(CH_2)_n$— or, when ==== is a single bond, also —$NHCO(CH_2)_n$— wherein n is an integer 0 to 4, m is 0, 1, or 2, $R_1$ is $C_{2-8}$-alkyl substituted by hydroxy, $C_{2-6}$-alkanoyloxy, 2-hydroxy-1,3-dioxolan-4-ylmethyl, 5-hydroxy-2,2-dimethyl-1,3-dioxepan-6-yl or $C_{1-6}$-alkylidenedioxy, $R_2$ independently is one of the $R_1$ groups, hydrogen or $C_{1-4}$-alkyl, $R_3$ and $R_4$ independently are $C_{1-4}$-alkyl, and $R_5$ and $R_6$ independently are $C_{1-4}$-alkyl or $C_{1-4}$-alkyl substituted by hydroxy, and scanning to obtain an MRI image.

2. A method of claim 1, wherein said compound is administered in admixture with a pharmaceutically acceptable carrier.

3. A method of claim 2, wherein B is a sugar residue.

4. A method of claim 2, wherein B is a protein residue.

5. A method of claim 4, wherein B is NR, $R_2$ and $R_1$ is $C_{2-4}$-alkyl substituted by hydroxy.

6. A method of claim 2, wherein B is a lipid residue.

7. A method of claim 2, wherein B is —$NR_1R_2$.

8. A method of claim 7, wherein $R_1$ is alkyl substituted by hydroxy.

9. A method of claim 7, wherein $R_1$ is $C_{2-6}$-alkanoyloxy or $C_{1-6}$-alkylidenedioxy.

10. A method of claim 2, wherein B is NR, $R_2$ and $R_1$ is $C_{2-4}$-alkyl substituted by hydroxy.

11. A method of claim 10, wherein X is —$(CH_2)_n$— and n is 0.

12. A method of claim 2, wherein m is 0 or 1.

13. A method of claim 2, wherein m is 2.

14. A method of claim 2, wherein when X is —$(CH_2)_n$—, n is 0 or 1.

15. A method of claim 2, wherein when X is —$NHCO(CH_2)_n$—, n is 2, 3 or 4.

16. A method of claim 2, wherein said compound is 2,2,5,5-tetramethyl-3-pyrroline-1-oxyl-3-carboxylic acid (2-hydroxyethyl)amide.

17. A method of claim 2, wherein said compound is 2,2,5,5-tetramethyl-3-pyrroline-1-oxyl-3-carboxylic acid (2,3-dihydroxypropyl)amide.

18. A method of claim 2, wherein said compound is of the formula

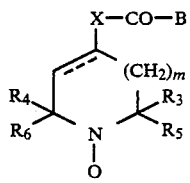

wherein

B is a pharmacologically acceptable, selectively binding protein, sugar, or lipid residue, or

----- is a single or double bond,
X is —$(CH_2)_n$— or when ----- is a single bond, also —$NHCO(CH_2)_n$ wherein n is an integer 0 to 4,
m is 0, 1, or 2,
$R_1$ is $C_{2-8}$-alkyl substituted by hydroxy, $C_{2-6}$-alkanoyloxy, 2-hydroxy-2-(2,2-dimethyl-1,3-dioxolan-4-yl)ethyl, 2,2-dimethyl-1,3-dioxolan-4-ylmethyl, 5-hydroxy-2,2-dimethyl-1,3-dioxepan-6-yl, or $C_{2-6}$-alkylidenedioxy,
$R_2$ independently is one of the $R_1$ groups, hydrogen or $C_{1-4}$-alkyl,
$R_3$ and $R_4$ independently are $C_{1-4}$-alkyl, and $R_5$ and $R_6$ independently are $C_{1-4}$-alkyl or $C_{1-4}$-alkyl substituted by hydroxy,
with the provisos that when $R_3$–$R_6$ are each methyl, ----- is a double bond, m is 0, X is —$(CH_2)_n$—, n is 0, B is —$NR_1R_2$ and $R_2$ is H, then $R_1$ is not 2-hydroxyethyl, 2,3-dihydroxypropyl or 1,1-dimethyl-2-hydroxyethyl; and when $R_5$ and $R_6$ are each alkyl, ----- is a double bond and m and are 0, then B is not a sugar residue.

19. A method of claim 18, wherein B is a sugar residue.

20. A method of claim 18, wherein B is a protein residue.

21. A method of claim 18, wherein B is albumin or an antibody.

22. A method of claim 21, wherein B is a monoclonal antibody.

23. A method of claim 18, wherein B is a lipid residue.

24. A method of claim 18, wherein B is —$NR_1R_2$.

25. A method of claim 24, wherein $R_1$ is alkyl substituted by hydroxy.

26. A method of claim 18, wherein m is 0 or 1.

27. A method of Claim 18, wherein when X is—$(CH_2)_n$—, n is 0 or 1.

28. A method of claim 18, wherein when X is —$NHCO(CH_2)_n$—, n is 2, 3 or 4.

29. A method of claim 18, wherein said compound is 2,2,5,5-tetramethylpyrrolidine-1-oxyl-3-carboxylic acid {2-hydroxy-2-(2,2-dimethyl-1,3-dioxolan-4-yl)ethyl}-amide,
2,2,5,5-tetramethylpyrrolidine-1-oxyl-3-carboxylic acid (1,3-dihydroxyprop-2-yl)amide,
2,2,5,5-tetramethyl-3-pyrroline-1-oxyl-3-carboxylic acid (2,2-dimethyl-1,3-dioxolan-4-ylmethyl)amide,
2,2,5,5-tetramethyl-3-pyrroline-1-oxyl-3-carboxylic acid {N-(2,2-dimethyl-1,3-dioxolan-4-ylmethyl)-N-methyl}amide,
2,2,5,5-tetramethyl-3-pyrroline-1-oxyl-3-carboxylic acid N-(2,3-dihydroxypropyl)-N-methylamide,
2,2,5,5-tetramethylpyrrolidine-1-oxyl-3-carboxylic acid (2,3,4-trihydroxybutyl)amide,
2,2,5,5-1-oxyl-3-carboxylic acid {N-(2,3,4,5,6-pentahydroxyhexyl)-N-methyl}-amide,
2,2,5,5-tetramethylpyrrolidine-1-oxyl-3-carboxylic acid (2,3-dihydroxypropyl)amide,
2,2,5,5-tetramethylpyrrolidine-1-oxyl-3-carboxylic acid bis(2-hydroxyethyl)amide,
2,2,5,5-tetramethylpyrrolidine-1-oxyl-3-carboxylic acid [N-(2,2-dimethyl-1,3-dioxolan-4-ylmethyl)-N-methyl]amide,
2,2,5,5-tetramethylpyrrolidine-1-oxyl-3-carboxylic acid N-(2,3-dihydroxypropyl)-N-methylamide,
2,2,5,5-tetramethyl-3-pyrroline-1-oxyl-3-carboxylic acid {2-hydroxy-2-(2,2-dimethyl-1,3-dioxolan-4-yl)ethyl}amide, 2,2,5,5-tetramethyl-3-pyrroline-1-oxyl-3-carboxylic acid (2,3,4-trihydroxybutyl)amide,
2,2,5,5-tetramethyl-3-pyrroline-1-oxyl-3-carboxylic acid (5-hydroxy-2,2-dimethyl-1,3-dioxepan-6-yl)amide,
2,2,5,5-tetramethyl-3-pyrroline-1-oxyl-3-carboxylic acid (1,3,4-trihydroxybut-2-yl)amide,
2,2,5,5-tetramethylpyrrolidine-1-oxyl-3-carboxylic acid (5-hydroxy-2,2-dimethyl-1,3-dioxepan-6-yl)amide,
2,2,5,5-tetramethylpyrrolidine-1-oxyl-3-carboxylic acid (1,3,4-trihydroxybut-2-yl)amide,
2,2,5,5-tetramethyl-3-pyrroline-1-oxyl-3-carboxylic acid {N-(2,3,4,5,6-pentahydroxyhexyl)-N-methyl}-amide,
2,2,5,5-tetramethyl-3-pyrroline-1-oxyl-3-carboxylic acid (1,3-dihydroxyprop-2-yl)amide,
2,2,5,5-tetramethyl-3-pyrroline-1-oxyl-3-carboxylic acid (5hydroxy-2,2-dimethyl-1,3-dioxepan-6-yl)amide,
succinic acid N-{2-hydroxy-2-(2,2-dimethyl-1,3-dioxolan-4-yl)ethyl}-N'-(2,2,6,6-tetramethyl-1-oxyl-piperidin-4-yl) diamide,
succinic acid {N-(2,2,6,6-tetramethyl-1-oxylpiperidin-4-yl)-N'-(2,3,4-trihydroxybutyl)} diamide,
(1-oxyl-2,2,6,6-tetramethylpiperidin-4-yl)-acetic acid {N-(2,3,4,5,6-pentahydroxyhexyl)-N-methyl}amide, or
succinic acid {N-(1-oxyl-2,2,5,5-tetramethylpyrrolidin-3-yl)-N'-methyl-N'-(2,3,4,5,6-pentahydroxyhexyl(} diamide.

30. A method of claim 1, wherein said compound is administered as a clathrate in a liposome.

* * * * *

UNITED STATES PATENT AND TRADEMARK OFFICE
CERTIFICATE OF CORRECTION

PATENT NO. : 4,925,652

DATED : May 15, 1990

INVENTOR(S) : Heinz GRIES et al.

It is certified that error appears in the above identified patent and that said Letters Patent is hereby corrected as shown below:

Column 22, claim 5, line 42:

reads " A method of claim 4, wherein B is NR, $R_2$ and $R_1$"

should read -- A method of claim 4, wherein B is $NR_1R_2$ and $R_1$ --

Column 22, claim 10, line 50:

reads "A method of claim 2, wherein B is NR, $R_2$ and $R_1$"

should read -- A method of claim 2, wherein B is $NR_1R_2$ and $R_1$ --

Signed and Sealed this

Fifteenth Day of October, 1991

*Attest:*

HARRY F. MANBECK, JR.

*Attesting Officer*  *Commissioner of Patents and Trademarks*